(12) United States Patent
Spraul et al.

(10) Patent No.: US 6,402,946 B1
(45) Date of Patent: Jun. 11, 2002

(54) DEVICE FOR FEEDING A CHROMATOGRAPHY FLOW

(75) Inventors: Manfred Spraul, Ettlingen; Martin Hofmann, Rheinstetten, both of (DE)

(73) Assignee: Bruker Analytik GmbH, Rheinstetten-Forcheim (DE)

( * ) Notice: Subject to any disclaimer, the term of this patent is extended or adjusted under 35 U.S.C. 154(b) by 57 days.

(21) Appl. No.: 09/697,673

(22) Filed: Oct. 26, 2000

(51) Int. Cl.7 .............................................. B01D 15/08
(52) U.S. Cl. ...................... 210/198.2; 210/659; 422/70; 73/61.56
(58) Field of Search ................................. 210/656, 659, 210/198.2; 422/70; 436/161; 73/61.52, 61.56, 61.57, 61.58

(56) References Cited

U.S. PATENT DOCUMENTS

| | | | | |
|---|---|---|---|---|
| 5,234,586 A | * | 8/1993 | Afeyan ..................... | 210/198.2 |
| 5,283,036 A | | 2/1994 | Hofmann et al. ............. | 422/70 |
| 5,827,946 A | * | 10/1998 | Klee ........................ | 210/198.2 |
| 6,090,280 A | * | 7/2000 | Connelly .................. | 210/198.2 |
| 6,106,710 A | * | 8/2000 | Fischer .................... | 210/198.2 |
| 6,139,734 A | * | 10/2000 | Settlage .................... | 210/198.2 |

FOREIGN PATENT DOCUMENTS

| | | | | |
|---|---|---|---|---|
| EP | 1 001 263 A1 | 5/2000 | .............. | 210/198.2 |

OTHER PUBLICATIONS

Combined HPLC, NMR Spectroscopoy, and Ion–Trap Mass Spectrometry with Application to the Detection and Characterization of Xenobiotic and Endogenous Metabolites in Human Urine, John P. Shockcor et al., *Anal. Chem.*, 1996, 68, 4431–4435.

Application of Directly Coupled High–Performance Liquid Chromatography–Nuclear Magnetic Resonance–Mass Spectrometry to the Detection and Characterisation of the Metabolites of 2–Bromo–4–trifluoromethylaniline in Rat Urine, Graeme B. Scarfe et al., *Analytical Communications*, Feb. 1997, vol. 34 (37–39).

* cited by examiner

*Primary Examiner*—Ernest G. Therkorn
(74) *Attorney, Agent, or Firm*—Weingarten, Schurgin, Gagnebin & Lebovici LLP

(57) ABSTRACT

A device for feeding a chromatography flow coming from a flow source, in particular from a liquid chromatography (LC) separating unit or a peak sampling or trapping unit, in part to at least a first decision detector unit and/or at least a first destination detector unit, and in part to at least a second destination detector unit is disclosed, including a first capillary line coming from the flow source, a second capillary line leading to the first decision detector unit, and/or to the first destination detector unit, and a third capillary line leading to the second destination detector unit, the first, second and third capillary line being connected with one another by means of a flow splitter splitting the flow coming from the first capillary line into two parts, a first part being fed into the second capillary line and the second part being fed into the third capillary line.

31 Claims, 5 Drawing Sheets

DEVICE FOR FEEDING A CHROMATOGRAPHY FLOW

BACKGROUND OF THE INVENTION

The present invention relates to a device for feeding a chromatography flow coming from a flow source, in particular from a liquid chromatography (LC) separating unit or a peak sampling or trapping unit, in part to at least a first decision detector unit and/or at least a first destination detector unit and in part to at least a second destination detector unit, comprising a first capillary line coming from the flow source, a second capillary line leading to the first decision detector unit and/or to the first destination detector unit, and a third capillary line leading to the second destination detector unit, the first, second and third capillary line being connected with one another by means of a flow splitter splitting the flow coming from the first capillary line into two parts, a first part being fed into the second capillary line and the second part being fed into the third capillary line.

The invention further relates to an apparatus for carrying out coupled liquid chromatography (LC) and at least two spectrometry measurements, comprising a LC separating unit, at least a first decision detector unit and at least a first destination detector unit and at least a second destination detector unit, in which the device mentioned before is used.

An apparatus and a device of the kind mentioned before, which are generally known are used in liquid chromatography (LC), in particular in high performance liquid chromatography (HPLC). Liquid chromatography is a known method for separating components of trace elements within liquid substrates to be analyzed.

Further, it is well-known to combine LC with nuclear magnetic resonance (NMR) spectroscopy measurements. The LC is used to separate components of a sample, which are selected in a LC detector, and the selected components were measured afterwards using NMR as the first destination detector unit. The coupling of LC with NMR is nowadays a well-known and accepted technique in science and industry.

For the technique of LC-NMR, four automation modes are known, as they are "on-flow", "stopped-flow", "time-slicing" and "loop-sampling".

In a pure on-line coupling, the NMR detector is directly coupled after the liquid chromatograph. In this on-line mode the separated peaks are fed from the LC continuously into the NMR detector to be spectrometrically examined on-line therein.

As an alternative to the on-line mode the stopped-flow technique is used, wherein the flow pump of the LC is stopped as long as a component is investigated inside the NMR detector.

The peak-sampling mode is a mode in which single separated peaks coming from the LC are selected and intermediately stored in a peak sampling unit for later successive investigation in the NMR detector.

The time-slicing mode is a clocked mode in which the LC peaks can be investigated in equally timed fractions to observe spectroscopic changes over a certain elution period.

Right from the beginning of commercializing the combined method of LC-NMR, the idea to hyphenate LC-NMR with additional sophisticated detection methods like mass spectroscopy (MS) as the second destination detector unit existed. Early attempts to combine LC-NMR with MS in 1996 have shown that the information obtained from such a combination was unsurpassed, in particular the selectivity of the peak selection of the LC peaks for further NMR investigation is increased substantially. As described by John P. Shockcor et al. in Anal.Chem. 1996, 68, 4431–4435, the advantage of combined LC-NMR-MS is that the structural information available from the complementary spectroscopic techniques provides rapid confirmation of the identity of the components of the sample.

Heretofore, in order to connect the LC-NMR system with the MS, in all cases just a flow splitter was hooked into the flow path, i.e. the flow splitter splits the flow coming from the first capillary line coming from the LC into two parts, the first part being fed into the second capillary line and the second part being fed into the third capillary line. The second capillary line leads to the LC detector as the first decision detector unit and/or the NMR detector as the first destination detector unit, while the third capillary line leads to the MS as the second destination detector unit. The split ratio between the first part of flow and the second part of flow varied from case to case between 50:1 and 20:1. The larger part of flow is used to feed the NMR detector, and the lower one for the more sensitive MS detector. In general, the users of the LC-NMR-MS system tried to adjust the timing for the MS such that the time a separated peak needed to reach the NMR was equal to or longer than the time to reach the MS.

Depending on the position of the splitter in the entire LC-NMR-MS system, it was possible to use the MS signal to trigger a stop of the chromatography for an NMR measurement, but not to use the MS signal to trigger the storage of the peak in a loop of the peak-sampling unit. All known systems, however, are restricted in the flexibility of their use. The known systems do not take into account that the time scales of the NMR measurements and the MS measurements are quite different. The NMR measurement runs on a time scale which is longer than the time scale of the MS measurements.

Whereas in the preceding description reference has been made to a coupled LC-NMR-MS system, the present invention is not restricted to such a combination, but can be used for other combinations of LC with at least two destination detectors, like for example infrared detectors or light-scattering detectors.

In the present description, a "decision detector" is to be understood as a detector, the signals of which are used for subsequent actions of the device or apparatus, while a "destination detector" is to be understood as a detector for detailed investigation and analysis of a sample peak.

It is therefore an object of the present invention to improve a device and an apparatus of the kind mentioned at the outset which allow a coupling of a flow source, in particular a LC separating unit with at least two detector units with a high degree of flexibility in using different modes of LC.

SUMMARY OF THE INVENTION

This object is achieved in terms of a device mentioned at the outset in that a first switchable valve means is provided which is connected to the third capillary line and to the second destination detector unit, which has at least two operating positions, wherein in at least a first group of at least one operating position the third capillary line is connected directly to the second destination detector unit, and wherein in at least one second group of at least one operating position the third capillary line is connected to at least one delay line.

By virtue of the first switchable valve means, the flexibility in use of the device according to the invention is advantageously increased. When the first valve means is in the at least one first operating position, the sample flow can quickly reach the second destination detector unit, for example a MS detector, so that the second destination detector unit signal can be used to trigger one of the LC modes which was not possible heretofore with the known systems. In other words, one of the dominant benefits of the present invention is that the second destination detector can advantageously be used as a decision detector for triggering subsequent actions of the device and/or apparatus. In particular, if the second detector unit comprises a MS detector, the high sensitivity of the MS signal can be used for triggering further action and choice of the LC mode, for example on-flow, stopped-flow or loop-sampling action, in particular for selecting peaks of interests from the sample flow. On the other hand, when the first valve means is in the at least one second operating position, this can be used for the sample flow to reach the second detector unit with a certain delay. This can be advantageously used in the on-flow mode in case that the delay is matched to the path from the splitter to the first detector unit, to simultaneously carry out measurements in the first destination detector unit and in the second destination detector unit and thus to have direct comparison of the on-flow data between the first destination detector unit and the second destination detector unit, e.g. a NMR detector and a MS detector. In the stopped-flow mode, the delay line can be used to intermediately park a sample peak therein for later investigation in the second destination detector unit. The flexibility of the device according to the invention, therefore, is highly enhanced.

In a preferred embodiment, the first decision detector unit comprises a chromatography (LC) detector, and the path from the Ad splitter to the second destination detector in the at least one first operating position of the first valve means is matched to the path from the splitter to the chromatography (LC) detector.

With this feature the first part of the sample flow and the second part of the sample flow reach the chromatography detector and the second destination detector unit substantially at the same time, wherein a small time difference in the range of a few seconds is not critical and can be compensated by a suited software. Both information coming from the chromatography detector and from the second destination detector unit can be advantageously combined to make decisions for further actions of the system. The advantage of this double information is an enhanced selectivity of the LC peak selection.

In a further preferred embodiment, the first destination detector unit comprises a spectrometry detector in which a measurement runs on a long-time scale compared to the second destination detector unit in the at least one second operating position of the first valve means, the third capillary line is connected to the second destination detector unit, and the path from the splitter to the second destination detector in the second operating position of the first valve means is matched to the path from the splitter to the first destination detector including the length of the flow cell of the first destination detector.

This feature has the advantage that a simultaneous on-flow measurement can be carried out in the first spectrometry detector, e.g. a NMR detector, and in the second destination detector unit, e.g. a MS detector, further having the advantage to be able to directly compare the on-flow data between the first spectrometric measurement and the second spectrometric measurement.

In a further preferred embodiment, in the at least one second operating position the third capillary line is disconnected from the second detector unit, while a further flow source, in particular a flow injection device, is connected to the second destination detector unit.

With this feature, in particular in case of a stopped-flow mode of the LC, while a measurement is carried out in the first destination detector unit, the second destination detector unit can be advantageously used to carry out further measurements on further sample peaks which are fed into the second destination detector unit from the second flow source. This feature is in particular useful in case that the first destination detector unit needs substantially more time to accumulate data than the second destination detector unit, because during the long-time measurement in the first destination detector unit several other measurements can be carried out in the second destination detector unit.

In a further preferred embodiment, at least one dilutor pump is connectable to the third capillary line for feeding at least one solvent into the third line.

This feature has the advantage that in the stopped-flow mode of the LC during a measurement in the first destination detector unit, one or more peaks parked in the at least one delay line can be fed into the second destination detector unit by means of the dilutor pump and a suited pushing solvent. By means of the dilutor pump, a flow rate for feeding the parked peak into the second destination detector unit can be chosen different from the flow rate generated by the chromatography pump. Furthermore, the sample flow in the third capillary line can be diluted or prepared for the measurement in the second destination detector unit by using suited solvents.

In this context it is preferred that the dilutor pump is connectable to and disconnectable from the third capillary line via second switchable valve means.

This feature enhances the flexibility of the device according to the present invention and allows full automation also in terms of feeding of the solvent into the third capillary line.

In a further preferred embodiment, in the at least one second operating position the third capillary line is connected to at least a second delay line.

The at least one second delay line, which may be chosen with a length different from the first delay line can be advantageously used to store a further peak before feeding same to the second destination detector unit.

In this context it is preferred that in the at least one second operating position of the first valve means the second delay line is connected to the first delay line, which in turn is connected to the third capillary line.

This feature has the advantage that two non-ideally separated chromatography peaks can be stored individually into the two delay lines, from which they can be fed into the second destination detector unit after one another with a suited time delay for a better investigation in the second destination detector unit.

In this context it is preferred that the first valve means is switchable in at least one operating position, in which the second delay line is disconnected from the first delay line.

This feature advantageously improves the possibility to separate two non-ideally separated chromatography peaks. By switching the first valve means into this operating position, the second delay line is disconnected from the first delay line, whereas the third capillary line is connected via the first delay line to the second destination detector unit so that the chromatography peak stored in the first delay line can be fed into the second destination detector unit. After having accomplished this operation, the first valve means can be switched into the at least one second operating position in order to push out the second chromatography peak into the second destination detector unit.

In a further preferred embodiment, the first valve means has at least one further operating position, in which the third capillary line is connected to a drain.

The advantage of this feature is that the chromatography pump can be used to clean parts of or the whole flow path of the device according to the present invention.

In a further preferred embodiment, the first valve means is configured as a turnable multiple port valve, in particular an 8-port valve.

This feature has the advantage that the first valve means is simple in terms of its structure and can be made on a low-cost basis. Further, by virtue of a turnable multiple port valve a simple switching mechanism between the different operating positions mentioned before is achieved.

In a further preferred embodiment, the valve comprises capillaries configured as engravings connecting pairs of the ports of the valve.

This feature has the advantage that the construction of the multiple port valve is further simplified.

Further, according to the present invention, an apparatus for carrying out coupled liquid chromatography (LC) and at least two spectrometry measurements is provided, which comprises a device according to one of the afore-mentioned embodiments.

In a further embodiment of the apparatus, it comprises a flow peak sampling unit for storing single separated peaks of the sample flow.

This feature allows an action to use the second detector unit, in particular in case the second detector unit comprises a MS detector, in the trigger mode to decide if a peak should be stored in a storage loop of the peak sampling unit and to investigate the stored peak later with the first detector unit, e.g. a NMR detector and again with the second detector unit. Further advantages of the peak sampling is the cutting function of cutting the sample flow, thereby increasing the selectivity and the sensitivity of the measurements compared to direct stopped flow measurements.

Such a peak sampling unit is known from U.S. Pat. No. 5,283,036, the disclosure of which is incorporated herein by reference.

In this context the peak-sampling unit can be combined with or replaced by means for concentrating up single peaks stored therein.

This feature has the advantage that the sharpness of single peaks can be increased, i.e. the width of the peaks can be decreased for a better investigation in the first or second detector unit.

In a further preferred embodiment the apparatus comprises control means for automatically or interactive controlling the device of one of the afore-mentioned embodiments.

This feature allows full automatic work of the device and of the entire apparatus as well as a manual interaction with the device.

As already mentioned before, one of the prominent features of the present invention is that the invention renders it possible to use the second destination detector unit, in particular in case that it is a MS detector, also as a decision detector unit for triggering different actions of the total device.

In a further aspect of the present invention, therefore, a method for conducting chromatography combined with spectroscopic measurements on a chromatography flow coming from a flow source in at least a first destination detector unit and in at least a second destination detector unit for spectrometrically investigating single peaks of the chromatography flow is disclosed, wherein at least the second destination detector unit is used as a decision detector unit for selecting peaks of interest, which later are spectrometrically investigated in the second destination detector unit.

By virtue of the method according to the present invention, a totally closed and fully automated chromatography work is possible without any interactions necessary.

In this context, it is useful to use the second destination detector unit as a decision detector for storing single peaks of interest in a peak sampling unit and to use the second destination detector later after transfer of single peaks of interest from loops of the peak sampling unit as an enhanced spectrometer.

In a further preferred embodiment, the first decision detector unit comprises a LC detector, and the first destination detector unit comprises a nuclear magnetic resonance (NMR) detector and the second destination detector unit comprises a mass spectrometer (MS) detector.

As already mentioned before, the present invention is not limited to this LC-NMR-MS system, although the present invention is in particular advantageous for the hyphenation of LC with NMR and MS.

Further features and advantages will be apparent from the following description and the attached drawings.

It will be understood that the above-mentioned features and those to be discussed below, are not only applicable in the given combinations, but may also be employed in other combinations or taken alone without departing from the scope of the present invention.

An embodiment of the invention is illustrated in the drawings and will be discussed in more detail below.

DETAILED DESCRIPTION OF A PREFERRED EMBODIMENT

Figure 1:
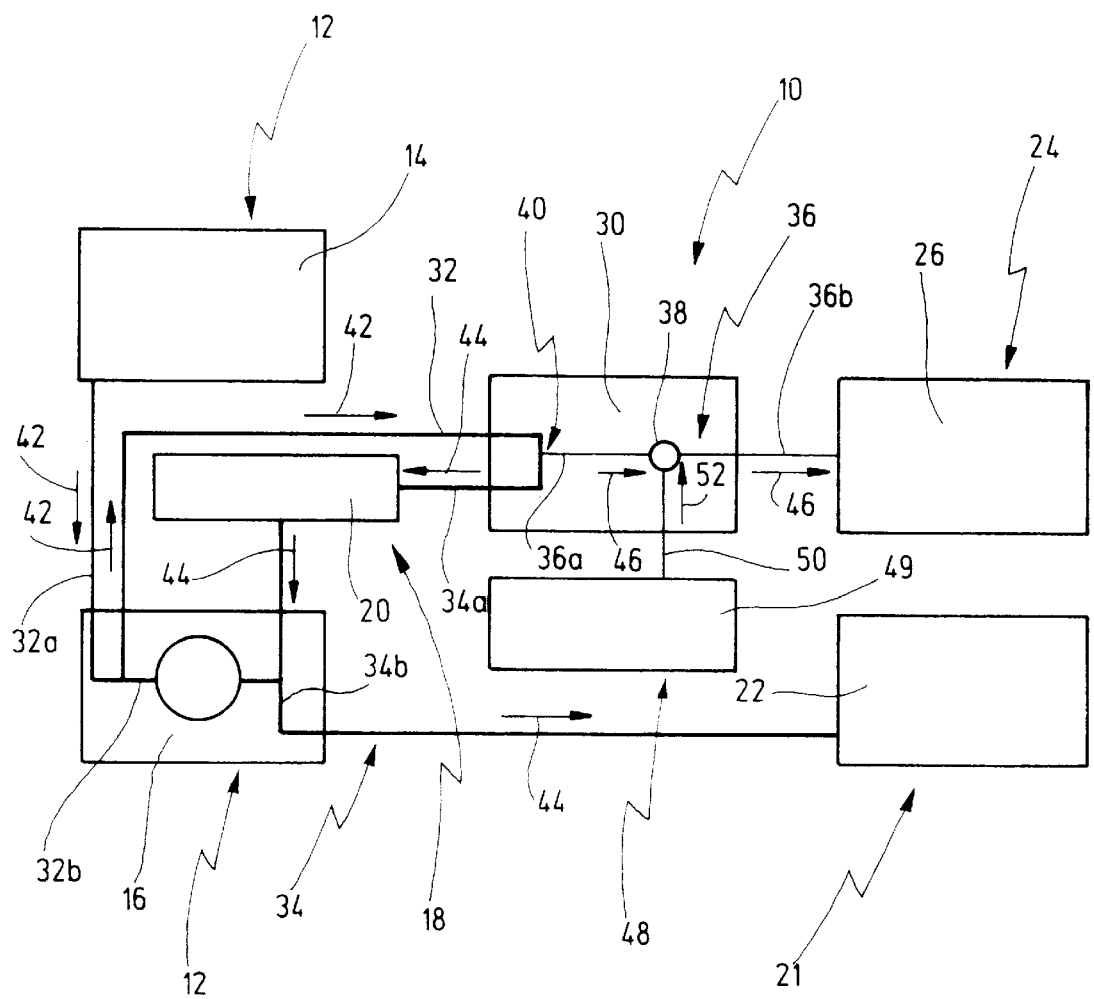
FIG. 1 is a block scheme of an apparatus according to the present invention.

In FIG. 1 an apparatus 10 for carrying out coupled liquid chromatography (LC) and at least two spectrometry measurements is shown in a block scheme. In the present embodiment, the apparatus 10 is adapted for carrying out liquid chromatography coupled with nuclear magnetic resonance (NMR) spectrometry and mass spectrometry (MS). Thus, the apparatus 10 is a LC-NMR-MS system.

The apparatus 10 generally comprises a flow source 12. The flow source 12 comprises a LC separating unit 14 for separating components in a liquid sample.

The flow source 12 further comprises a peak sampling unit 16 comprising a plurality of storage loops (not shown) for storing one or more chromatography peaks. The peak sampling unit 16 can also be combined with or replaced by means for concentrating up single peaks stored therein.

The apparatus 10 further comprises a first decision detector unit 18. The first decision detector unit 18 comprises a LC detector 20, which generally works in the UV/VIS range.

The apparatus further comprises a first destination detector unit 21, a NMR detector 22 comprising a flow probe.

The LC detector 20 and the NMR detector 22 are coupled to the LC separating unit 14 as will be described hereinafter.

A second destination detector unit 24 comprises a MS detector 26. Preferably the MS detector 26 has fragmentation capabilities so that $MS^n$ investigations are possible.

The second destination detector unit 24 comprising the MS detector 26 is connected to the flow source 12 as will be described in more detail below.

The apparatus 10 further comprises a device 30 according to the present invention for feeding a chromatography sample flow coming from the flow source 12, in the present case from the LC unit 14 and/or from the peak sampling unit 16 in part to the first decision detector unit 18 and/or the first destination detector unit 21 and in part to the second destination detector unit 24.

The device 30 comprises a first capillary line 32 coming from the flow source 12. The first capillary line 32 is connected to the LC separating unit 14, i.e. to the separating column thereof via a portion 32a of the capillary line 32, and to the peak sampling unit 16 via a portion 32b of the capillary line 32.

The device 30 further comprises a second capillary line 34 connected to the first capillary line 32 and leading to the first decision detector unit 18 and to the first destination detector unit 21. A portion 34a of the second capillary line 34 leads from the first capillary line 32 to the LC detector 20 from which a portion 34b of the second capillary line 34 leads to the NMR detector 22.

A third capillary line 36 is connected to the first capillary line 32 via a portion 36a and to the second destination detector unit 24 via a portion 36b.

A first switchable valve means 38 which will be described in more detail hereinafter, is disposed in the third capillary line 36.

All capillary lines mentioned before and those to be discussed below have small inner bores, preferably a maximum inner diameter of 0.25 mm, in order to avoid chromatography peak broadening, which would lower the sensitivity of the measurements in the first and second decision and destination detector units 18, 21 and 24.

Further, a flow splitter 40 is provided with the device 30 for splitting the flow coming from the first capillary line 32 into two parts, the first part being fed into the second capillary line 34 and the second part being fed into the third capillary line 36. The flow coming from the flow source 12 is indicated by arrows 42, the first part of flow flowing in the second capillary line 34 is indicated by arrows 44 and the second part of flow flowing in the third capillary line 36 is indicated by arrows 46.

The splitter 40 can be fixed or free adjustable. The splitter 40 must only meet the requirements to split the flow coming from the flow source 12 in a suited ratio and to provide an exact flow after the split in the second capillary line 34 and the third capillary line 36 also with LC gradients.

The split ratio is preferably chosen as 20:1, wherein the major part of the flow is fed into the second capillary line 34 and the minor part in the third capillary line 36.

The apparatus 10 further comprises a second flow source 48 herein form of a flow injection device 49. The second flow source 48 is connected to the third capillary line 36 via the first switchable valve means 38 by a capillary line 50. From the flow injection device 48 a sample flow indicated by an arrow 52 can be fed via the switchable valve means 38 to the second destination detector unit 24.

The apparatus 10 further comprises a not shown drain to a waste.

Figure 2:
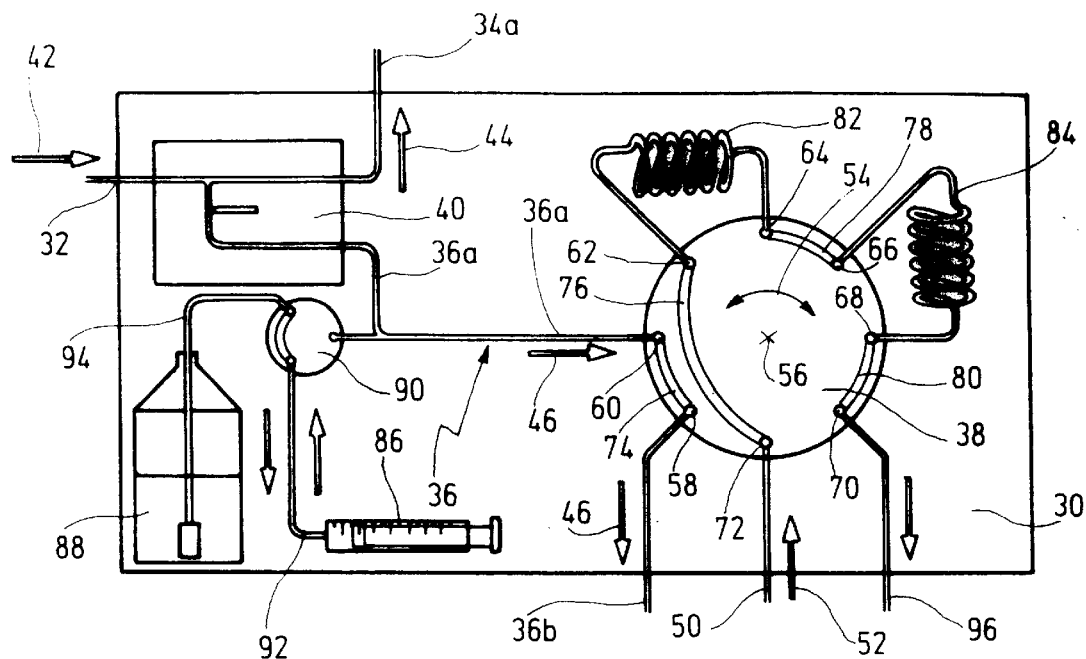
FIG. 2 is a scheme of a device according to the present invention used in the apparatus in FIG. 1 in an operating position as one example of the first group of operating positions.

Referring now to FIG. 2, the device 30 with further details is shown in an enlarged scale with respect to FIG. 1.

The first switchable valve means 38 is configured as a turnable multiple port valve, which can be switched between different operating positions by turning the valve body in either directions of a double arrow 54 about a center axis 56.

The first switchable valve means is in the present embodiment an 8-port valve having eight ports 58–72.

The pairs of ports 58, 60; 64, 66; 68, 70 and 62, 72 are connected to one another through engravings 74–80. The engravings 74–80 from capillaries for the sample flow passing there-through.

In its entirety, the first switchable valve means 38 has a low dead volume to avoid chromatography peak broadening as discussed before in connection with the capillary lines.

Further, a first delay line 82 is disposed at the first valve means 38 as well as a second delay line 84. The delay lines 82 and 84 are configured as loops connected to the first valve means 38.

The device 30 further comprises at least one dilutor pump 86 preferably having more than two syringe pumps. In FIGS. 2 through 9 only one syringe pump is depicted.

The dilutor pump 86 is connected to a solvent vessel 88 which forms a reservoir for a solvent. Again, whereas only one solvent vessel 88 with one solvent is depicted in the figures, situations are conceivable where four or more different solvents can be used.

A second switchable valve means 90 is provided either to connect the dilutor pump 86 to the solvent vessel 88 or to connect the dilutor pump 86 to the third capillary line 36 via a T-piece. The second switchable valve means 90 again is a turnable multiple port valve, in the present case where one dilutor pump 86 and one solvent vessel 88 is provided, it is a 3-port valve, wherein two ports of the valve means 90 are connected to each other by an engraving.

A line 92 connects the dilutor pump 86 to the second valve means 90, and a line 94 connects the solvent vessel 88 to the second valve means 90.

Finally, a line 96 leading to the not shown drain or waste is connected to the first valve means 38.

The apparatus 10 comprises control means for controlling the device 30, i.e. all switchable parts of the device 30, automatically under external software control, whereas an interaction via a keypad for all actions is possible, too.

In the following different operating positions of the device 30 are described.

FIG. 2 shows the device 30 in one of a group of first operating positions, in which the third capillary line 36 is connected directly to the second destination detector unit 24, i.e. to the MS detector 26. The second part of flow, which is minor than the first part of flow of the sample flow is going through the portion 36a of the third capillary line 36 via the port 60, the engraving 74 and the port 58 and through the portion 36b of the third capillary line 36 directly to the MS detector 26.

As the device 30 is preferably connected directly after the separation column of the LC separating unit 14, the separated chromatography peaks will reach the MS detector 26 very quickly. The first part of the flow according to the arrow 44 of the sample flow is led via the second capillary line 34 to the LC detector 20 and/or the NMR detector 22.

The path or the distance from the splitter 40 to the second destination detector unit 24 is matched to the path or distance from the splitter 40 to the LC detector 20 such that the major part of the chromatography peak will roughly need the same time to reach the LC detector 20 as the minor part of the peak to reach the MS detector 26. A small time difference in the range of a few seconds is uncritical.

In this case, having a suited software, the information coming from the MS detector 26 and from the LC detector 20 can be used to make decisions for further actions in different modes. These decisions can be carried out with an AND/OR logic. The software preferably combines the information coming from the LC detector 20 and the MS detector 26 and is able to compensate the time difference resulting from the different flow times to each detection source. It is possible to process more than two signals when multiple channels are used.

The flow injection device 49 is connected via the capillary line 50, the port 72, the engraving 76, the port 62 with the delay line 82 and further via the port 64, the engraving 78, the port 66 with the delay line 84 and further via the port 68, the engraving 80, and the port 70 with the line 96 to the drain. In this operation position the flow injection device 49 can be used to clean the flow path and/or to prepare it for further LC-NMR/MS work. It is also thinkable to use the flow injection device 49 to park a sample in the delay line 82 and/or the delay line 84 for later investigations with the MS detector 26.

Based on the information coming from the MS detector 26 and/or from the LC detector 20, the following actions can be triggered: no action, if certain set values are not fulfilled, stopping the chromatography when the found peak is in the center of the flow cell of the NMR detector 22, parking the peak in a storage loop of the peak sampling unit 16 for later investigations either with the NMR detector 22 plus enhanced $MS^n$ investigations, or going to the time-slicing mode by direct stopped-flow or multiple loop collection.

If the second valve means 90 is switched into a operating position to connect the dilutor pump 86 via capillary line 92 with the third capillary line 36 (like in FIG. 7), an add-up flow will be possible. To use a so-called "add-up flow" can have several reasons: a first reason is that the sample is too concentrated for the MS detector 26 and has to be diluted further; a second reason is that the ionization strength of the separation solvent in the LC separating unit 14 is not good enough for the MS detector 26 and therefore an ionizing helping agent should be added; a third reason is that a deuterium back-exchange is needed to have a better comparison with known protonated data out of standard MS measurements (LC-NMR typically uses $D_2O$ instead of $H_2O$, which can lead to a mass distribution if the molecule has exchangeable protons).

Figure 3:
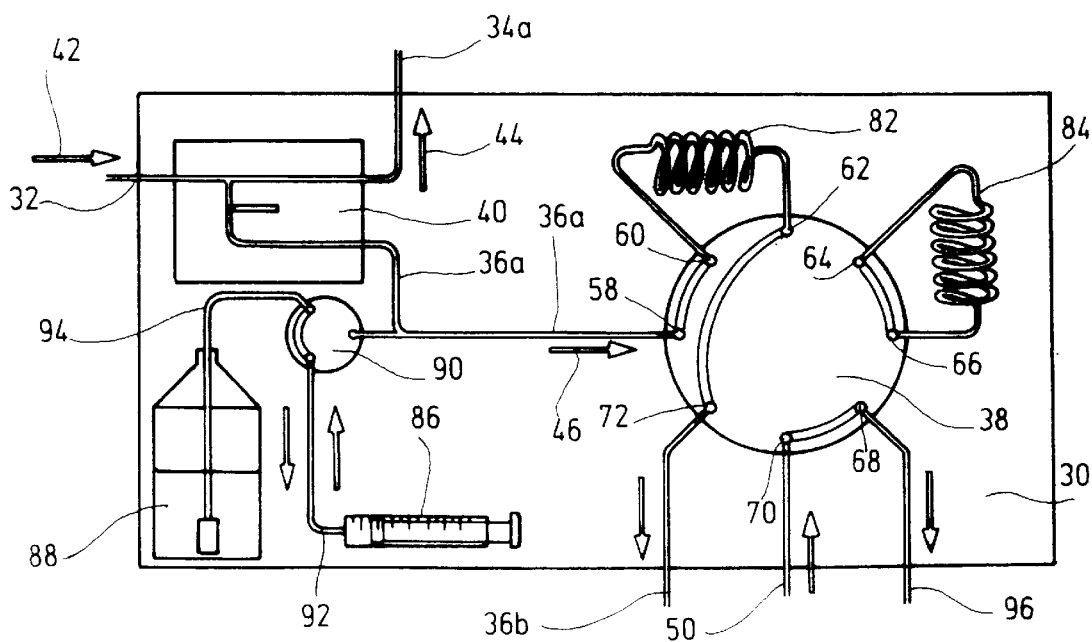
FIG. 3 is a scheme of the device of FIG. 2 in another operating position as one example of the second group of operating positions.

Referring now to FIG. 3, the first switchable valve means 38 has been turned into another operating position. This operating position of the first switchable valve means 38 is one of a second group of operating positions, in which the third capillary line 36 is connected to at least one delay line, in the present case to the delay line 82. In this case peaks, coming from the flow source 12 will reach the MS detector 26 with a certain delay with respect to the LC detector 20. This means that the major part of the peak will reach the LC detector 20 before the minor part of the peak will be in the MS detector so that the signal from the LC detector 20 can be used for triggering further action.

If the MS detector 26 is a detector with fragmentation ability like ion trap, time of flight, quadrupole-MS, Fourier transformation MS, etc., multiple $MS^n$ investigation is possible.

The operating position shown in FIG. 3 can be used in case of an on-flow action. If namely the path from the splitter 40 to the second detector unit 24 is matched to the path from the splitter 40 to the NMR detector 22 and also is matched to the length of the flow cell of the NMR detector 22, then a direct comparison of the on-flow data between the MS detector 26 and the NMR detector 22 is possible.

According to FIG. 3, the flow injection device 48 is directly connected to the drain via capillary line 96. Again, the flow injection device 49 can be used to clean the flow path.

Figure 4:
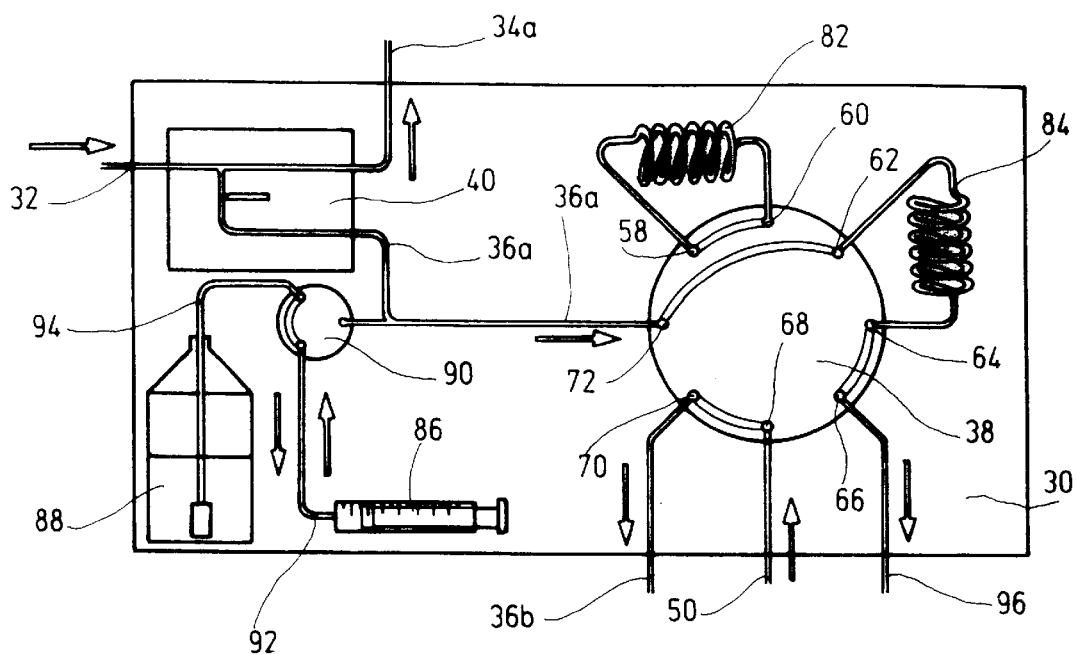
FIG. 4 is a scheme of the device in FIG. 2 in still another operating position as a further example of the second group of operating positions.

Referring now to FIG. 4, the first valve means 38 has been turned to another operating position of the second group of operation positions, in which the third capillary line 36, i.e. the portion 36a of the third capillary line 36 is connected to the second delay line 84, which in turn is connected to the drain via the capillary line 96.

This operating position can be used for the transfer of a sampled peak from the peak sampling unit 16 or for the stopped-flow mode wherein on stopping the chromatography pump, a peak of the sample flow going through the third capillary line 36 can be parked in the second delay line 84. The stopped-flow action is triggered on the basis of a signal from the LC detector 20, because the sample flow going through the third capillary line cannot reach the MS detector 26 at the same time as the major part reaches the LC detector 20.

Figure 7:
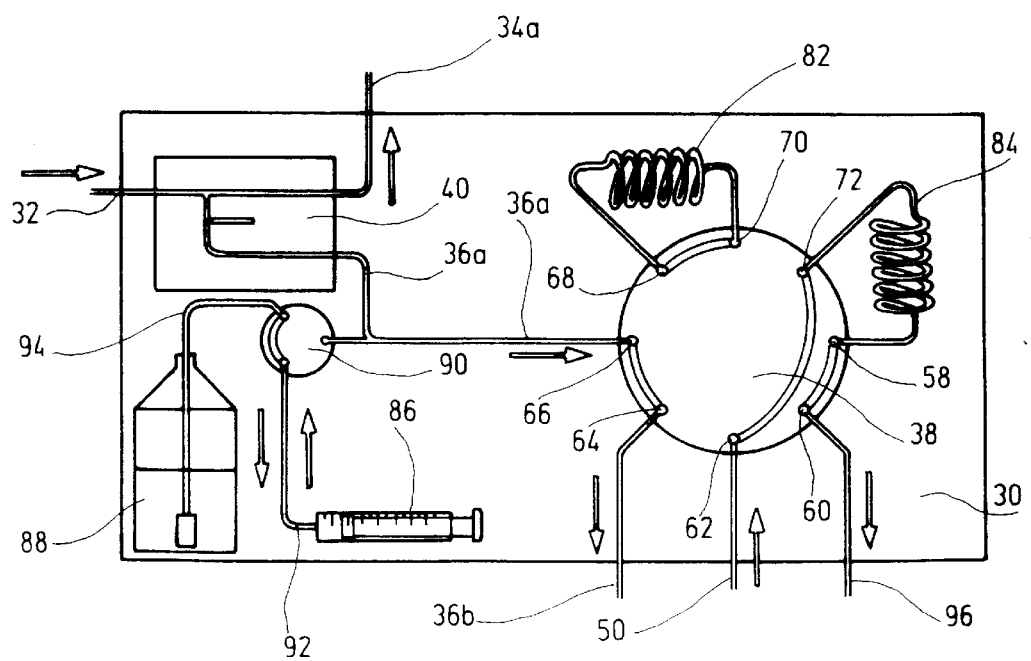
FIG. 7 is a scheme of the device in FIG. 2 in still another operating position as a further example of the first group of operating positions.

By switching the first valve means 38 now into the operating position shown in FIG. 7, the peak parked in the second delay line 84 can be fed to the MS detector 26 by connecting the dilutor pump 86 to the third capillary line 36. The peak now can be fed with a very low flow rate to the MS detector. Again, in case the MS detector 26 has fragmentation capabilities, $MS^n$ investigations are possible.

Further, if the size of the second delay line 84 is chosen other than for the first delay line 82, e.g. if the size of the second delay line is chosen in a way that it will be larger than the dead volume to the flow cell of the NMR detector 22, then a chromatography based stopped-flow action can be carried out. In this case, the chromatography will not stop immediately, but with a certain delay. This delay is calculated such that the major part of the peak for the investigation will be in the flow cell of the NMR detector 22 and the minor part in the second delay line 84 of the device 30.

Further referring to FIG. 4, the flow injection device 48 is directly connected to the MS detector 26, whereas the third capillary line 36 is disconnected from the second detector unit 24. Thus, the flow injection device 49 can be used to transfer peaks directly to the MS detector 26. This position can be applied to use the NMR measurement time after a stopped-flow action so that, assuming that the NMR measurement needs substantially more time than the MS measurement to accumulate its data, this waiting period can be used for flow-injection actions or another separation.

Alternatively, the flow-injection device 49 can be used to inject a suited solvent into the MS detector 26 to avoid that the MS detector 26 runs dry.

Figure 5:
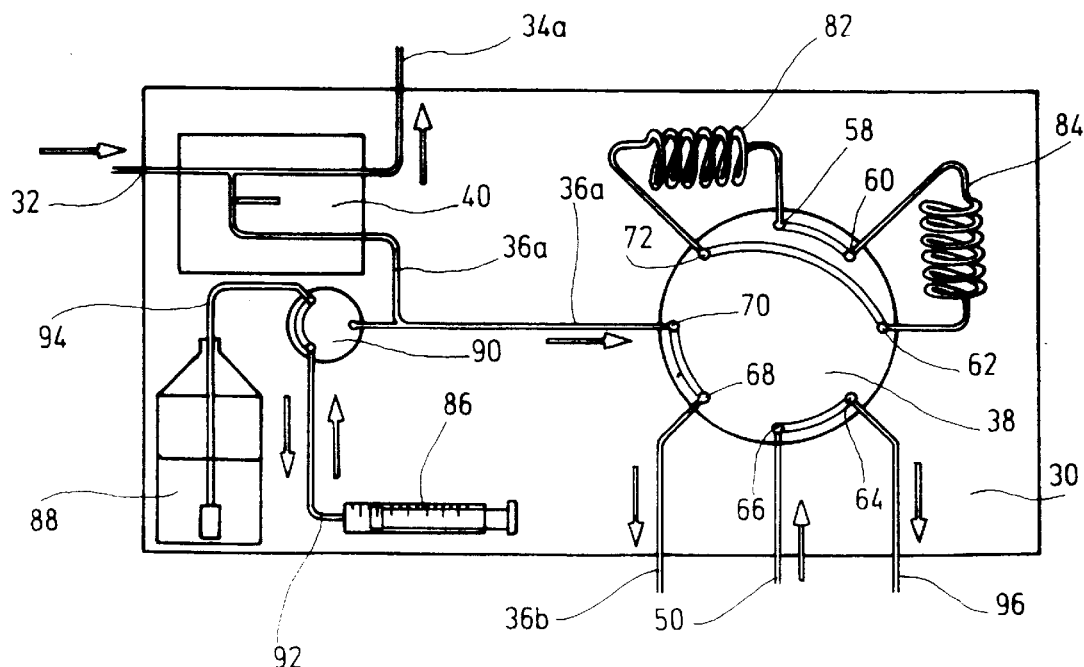
FIG. 5 is a scheme of the device in FIG. 2 in still another operating position as a further example of the first group of operating positions.

In FIG. 5, the first valve means 38 is shown in an operating position corresponding to the first group of operating positions as in FIG. 2, in which the third capillary line 36 is directly connected to the MS detector 26. The flow-injection device 49, however, is directly connected to the drain. The first delay line 82 and the second delay line 84 are short-circuited without any flow therebetween.

Figure 6:
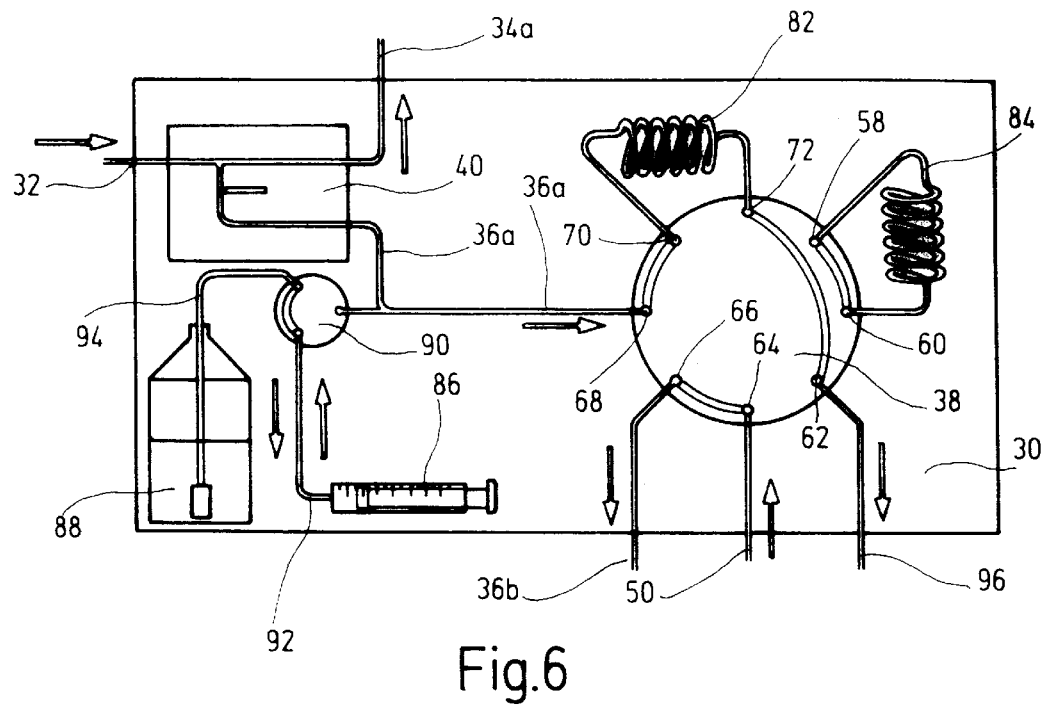
FIG. 6 is a scheme of the device in FIG. 2 in still another operating position as a further example of the second group of operating positions.

The operating position of the first valve means 38 shown in FIG. 6 is similar to the operating position of first valve means 38 in FIG. 4, with the difference that the third capillary line 36 is connected to the drain via the first delay line 82 instead of the second delay line 84. This operating position of the first valve means 38 is a further operating position of the second group of operating positions. A peak can be parked in the delay line 82 and by switching to the position in FIG. 3 can be fed into the MS detector 26.

In FIG. 7, the first valve means 38 is shown in a further operating position of the first group of operating positions like in FIG. 2, in which the third capillary line 36 is directly connected to the MS detector 26. The difference between the operating position of FIG. 7 and the operating position of FIG. 2 is that the flow injection device 48 is connected to the drain via the second delay line 84 only.

Figure 8:
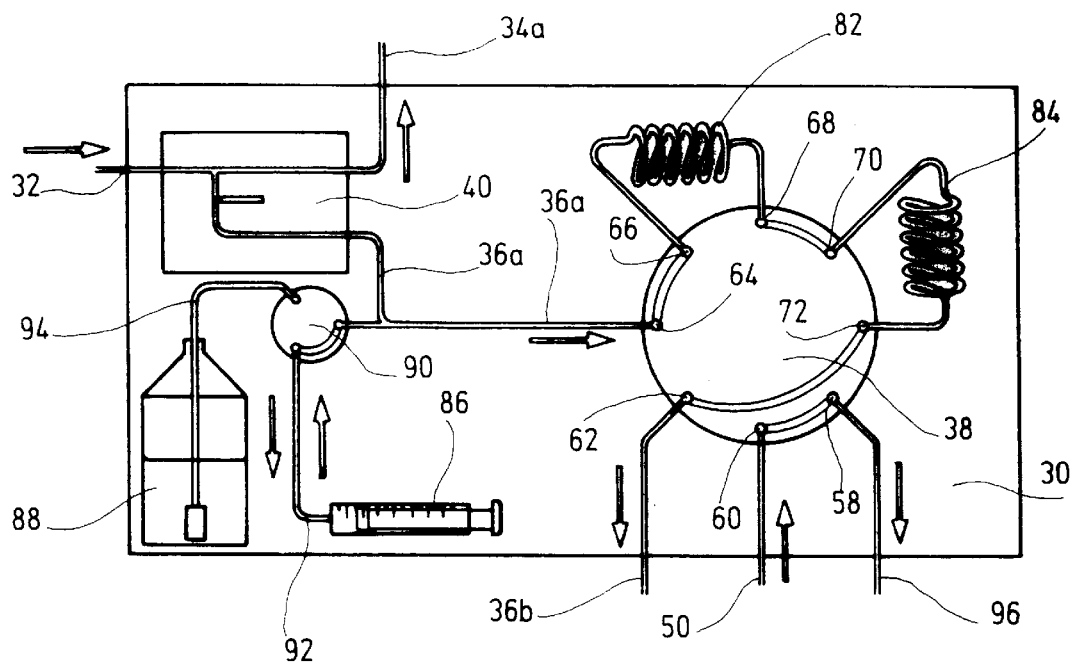
FIG. 8 is a scheme of the device in FIG. 2 in still another operating position as a further example of the second group of operating positions.

Referring now to FIG. 8, there is shown a further operating position of the first valve means 38 according to the second group of operating positions, in which the third capillary line is connected to both the first delay line 82 and the second delay line 84, wherein it is further connected to the MS detector 26.

This operating position is helpful in case that two non-ideally separated chromatography peaks come from the LC unit 14. The two peaks can be parked individually into the first delay line 82 and in the second delay line 84, and by switching the first valve means 38 into the operating position of FIG. 3, as soon as the first peak has filled the first delay line 82, the peaks are separated and can be emptied one after the other using the dilutor pump 86 in the afore-mentioned way.

Figure 9:
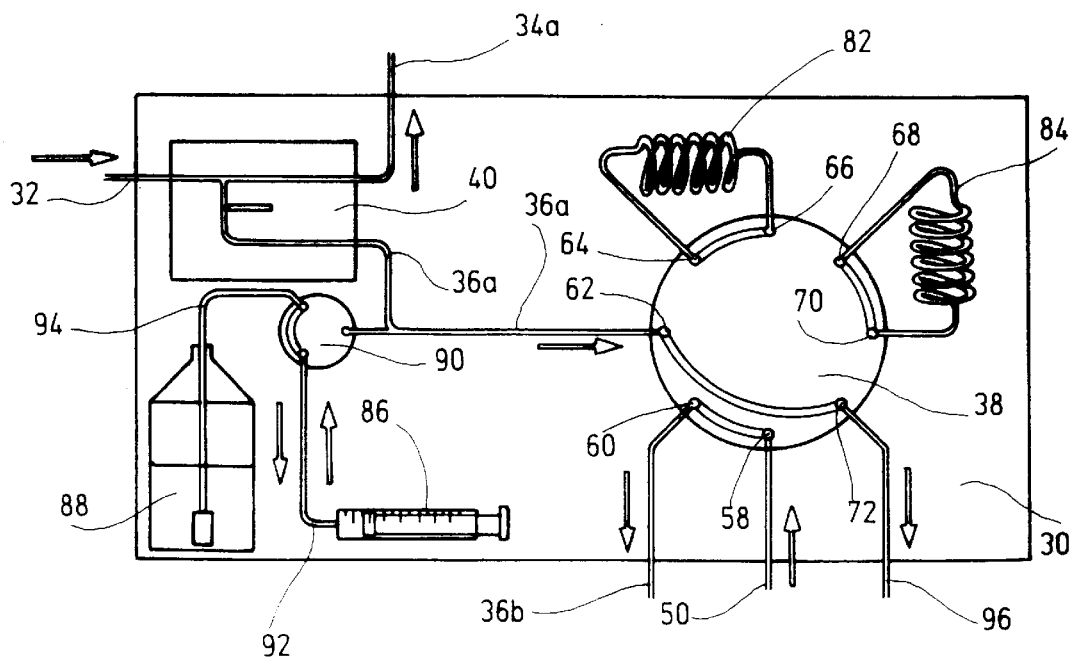
FIG. 9 is a scheme of the device in FIG. 2 in still another operating position.

Finally, in FIG. 9, the third capillary line 36 is connected via the port 62, the engraving 76 and the port 72 via the capillary line 96 to the drain. This operating position of the first valve means 38 can be used as the initial operating position of the device 30. Using the chromatography pump, cleaning of the flow path can be carried out.

In this operating position, the flow injection device 48 again is connected to the MS detector 26 directly.

In the following, one typical work flow for peak sampling based on MS information and the transfer of peaks to the NMR detector 22 and the MS detector 26 will be described as an example of the function of the apparatus 10 and the device 30. Using the MS information first as a decision maker to trigger the peak sampling and then to get more detailed MS information in the transfer step is advantageous.

At the beginning, the device 30 is switched to the operating position shown in FIG. 2.

In a first step, the chromatography is running. The flow is directed through the splitter 40 to the MS detector 26 and to the LC detector 20. The dead volumes from the splitter 40 to the MS detector 26 and from the splitter 40 to the LC detector are adjusted to be about the same as already mentioned before. Slight differences can be corrected via software, so that the signal of the same compound will appear in the data acquisition software on either channel at the same time. A suited data acquisition software with on-line, in-time automatic detection possibilities on several channels simultaneously, will calculate on the incoming data from the MS detector 26 and the LC detector 20 or other analog sources.

Based on the set auto-detection values, time windows, signal height, and thresholds, and using the AND/OR-logic on the different signal channels, the sampling action will be initiated. Is a signal or are signals coming from the MS detector 26 and/or the LC detector 20 fulfilling the criteria, the peak will be directed into a loop of the peak sampling unit 16 and will be parked there for later investigations. If the chromatography separation is finished and all of the interesting peaks are parked in loops of the peak sampling unit 16, the next step can be started manually or in an automatic way.

For the second step, the device 30 is switched to the operating position shown in FIG. 4. One of the peaks in the loops is chosen to be investigated more intensively by the NMR detector 22 and the MS detector 26. Bypassing the separation column of the LC unit 14, the parked peak will be pumped out of the loop of the peak sampling unit 16 and will be directed now to the NMR detector 22, but again via the splitter 40. Due to the second delay line 84, the split minor part to the MS detector 26 needs longer to pass the capillaries than the major part, which will be stopped reaching the NMR detector 22, i.e. the measurement cell thereof. In stopping the chromatography pump to get the possibility of a longer NMR measurement, the minor part of the compound will be parked again in the second delay line 84 of the device 30. The NMR detector 22 will start the measurement and the device 30 will go to the next step.

In the third step, the device 30 is switched into the operating position shown in FIG. 8.

Now, the dilutor pump 86 starts to pump in a very low speed (e.g. 5 µl/min to 20 µl/min), the minor peak part slowly to the MS detector 26. The low pumping speed allows to enhance the time of investigation of a 20 second wide peak to 3 to 5 minutes. With a suited MS detector 26, various experiments can be done during several minutes, e.g. positive-negative ion switching and the fragmentation to $MS^n$, in order to name only some of the possibilities.

After finishing the NMR and the MS measurements, the device 30 will be repeatedly switched between the position shown in FIG. 4 and the position shown in FIG. 8 in order to carry out the afore-mentioned second and third steps until all interesting peaks out of the loops of the peak sampling unit 16 have been investigated.

What is claimed is:

1. A device for feeding a chromatography flow coming from a flow source, selected from a liquid chromatography (LC) separating unit or a peak sampling or trapping unit, in part to at least a first decision detector unit and/or at least a first destination detector unit and in part to a second destination detector unit, comprising:

a first capillary line coming from said flow source, a second capillary line leading to said first decision detector unit and/or to said first destination detector unit, a third capillary line leading to said second destination detector unit, a flow splitter connecting said first, second and third capillary line with one another and splitting maid flow coming form said first capillary line into two parts, a first part being fed into said second capillary line and a second part being fed into said third capillary line, a first switchable valve means connected to said third capillary line and to said second destination detector unit, wherein said first switchable valve means has at least two operating positions, wherein in at least a first operating position said third capillary line is connected directly to said second destination detector unit, and wherein in at least a second operating position said third capillary line is connected to at least one delay line.

2. The device of claim 1, wherein said first decision detector unit comprises a chromatography (LC) detector, and a path from said splitter to said second destination detector unit in said at least one first operating position of said first valve means is matched to a path from said splitter to said chromatography (LC) detector.

3. The device of claim 1, wherein said first destination detector unit comprises a spectrometry detector in which a measurement runs on a long-time scale compared to the second destination detector unit, and, in said at least one second operating position of said first valve means, said first capillary line is connected to said second destination detector unit, and a path from said splitter to said second destination detector is matched to a path from said splitter to said first detector including the length of a flow cell of said first destination detector unit.

4. The device of claim 1, wherein in said at least one second operating position of said first valve means the third capillary line (36) is disconnected from said second destination detector unit, while a flow injection device is connected to said second destination detector unit.

5. The device of claim 1, wherein at least one dilutor pump is connectable to said third capillary line for feeding at least one solvent into said third capillary line.

6. The device of claim 5, wherein said dilutor pump is connectable to and disconnectable from said third capillary line via a second switchable valve means.

7. The device of claim 1, wherein in said at least one second operating position of said first valve means, said third capillary line is connected to at least a second delay line.

8. The device of claim 7, wherein, in said at least one second operating position of said first valve means, said second delay line is connected to said first delay line, which in turn is connected to said third capillary line.

9. The device of claim 8, wherein said first valve means is switchable in at least one operating position, in which said second delay line is disconnected from said first delay line.

10. The device of claim 1, wherein said first valve means has at least one further operating position, in which said third capillary line is connected to a drain.

11. The device of claim 1, wherein said first valve means is configured as a turnable multiple port valve.

12. The device of claim 11, wherein said turnable multiple port valve is an 8-port valve.

13. The device of claim 12, wherein said 8-port valve comprises capillaries configured as engraving connecting pairs of said ports of said valve.

14. An apparatus for carrying out coupled liquid chromatography (LC) and at least two spectrometry measurements, comprising a LC separating unit, at least a first decision detector unit and/or at least a first destination detector unit and at least a second destination detector unit, comprising a device for feeding a chromatography flow coming from a flow source, selected from a liquid chromatography (LC) separating unit or a peak sampling or trapping unit, in part to at least a first decision detector unit and/or at least a first destination detector unit and in part to a second destination detector unit, comprising:

a first capillary line coming from said flow source, a second capillary line leading to said first decision detector unit and/or to said first destination detector unit, a third capillary line leading to said second destination detector unit, a flow splitter connecting said first, second and third capillary line with one another and splitting said flow coming form said first capillary line into two parts, a first part being fed into said second capillary line and a second part being fed into said third capillary line, a first switchable valve means connected to said third capillary line and to said second destination detector unit, wherein said first switchable valve means has at least two operating positions, wherein in at least a first operating position said third capillary line is connected directly to said second destination detector unit, and wherein in at least a second operating position said third capillary line is connected to at least one delay line.

15. The apparatus of claim 14, wherein it further comprises a peak sampling unit for storing single separated peaks of said chromatography flow.

16. The apparatus of claim 15, wherein said peak sampling unit is combined with or replaced by means for concentrating up single peaks stored therein.

17. The apparatus of claim 14, wherein it further comprises control means for automatically or interactive controlling said device for feeding said chromatography flow.

18. The apparatus of claim 14, wherein said first decision detector unit comprises an LC detector, said first destination detector unit comprises a nuclear magnetic resonance (NMR) detector and said second destination detector unit comprises a mass spectrometer (MS).

19. The apparatus of claim 18, wherein said mass spectrometer (MS) detector comprises fragmentation ability.

20. The apparatus of claim 14, wherein said first decision detector unit comprises a chromatography (LC) detector, and a path from said splitter to said second destination detector unit in said at least one first operating position of said first valve means is matched to a path from said splitter to said chromatography (LC) detector.

21. The apparatus of claim 14, wherein said first destination detector unit comprises a spectrometry detector in which a measurement runs on a long-time scale compared to the second destination detector unit, and, in said at least one second operating position of said first valve means, said first capillary line is connected to said second destination detector unit, and a path from said splitter to said second destination detector is matched to a path from said splitter to said first detector including the length of a flow cell of said first destination detector unit.

22. The apparatus of claim 14, wherein in said at least one second operating position of said first valve means the third capillary line (36) is disconnected from said second destination detector unit, while a flow injection device is connected to said destination detector unit.

23. The apparatus of claim 14, wherein at least one dilutor pump is connectable to said third capillary line for feeding at least one solvent into said third capillary line.

24. The apparatus of claim 23, wherein said dilutor pump is connectable to and disconnectable from said third capillary line via a second switchable valve means.

25. The apparatus of claim 14, wherein in said at least one second operating position of said first valve means, said third capillary line is connected to at least a second delay line.

26. The apparatus of claim 25, wherein, in said at least one second operating position of said first valve means, said second delay line is connected to said first delay line, which in turn is connected to said third capillary line.

27. The apparatus of claim 26, wherein said first valve means is switchable in at least one operating position, in which said second delay line is disconnected from said first delay line.

28. The apparatus of claim 14, wherein said first valve means has at least one further operating position, in which said third capillary line is connected to a drain.

29. The apparatus of claim 14, wherein said first valve means is configured as a turnable multiple port valve.

30. The apparatus of claim 29, wherein said turnable multiple port valve is an 8-port valve.

31. The apparatus of claim 30, wherein said 8-port valve comprises capillaries configured as engravings connecting pairs of said ports of said valve.

* * * * *

UNITED STATES PATENT AND TRADEMARK OFFICE
CERTIFICATE OF CORRECTION

PATENT NO. : 6,402,946 B1
DATED : June 11, 2002
INVENTOR(S) : Manfred Spraul et al.

It is certified that error appears in the above-identified patent and that said Letters Patent is hereby corrected as shown below:

<u>Title page,</u>
Item [73], Assignee, "Bruker Analytik GmbH," should read
-- Bruker Analytik GMBH, --;

<u>Column 3,</u>
Line 33, "the Ad splitter" should read -- the splitter --;

<u>Column 13,</u>
Line 2, "maid" should read -- said --.

Signed and Sealed this

Fourth Day of November, 2003

JAMES E. ROGAN
*Director of the United States Patent and Trademark Office*